United States Patent [19]

Dunski et al.

[11] Patent Number: 4,569,959
[45] Date of Patent: Feb. 11, 1986

[54] ISOCYANURATE ESTERS OF THIOAMIDOPHENOLS AND POLYOLEFIN POLYMERIC COMPOSITIONS STABILIZED THEREWITH

[75] Inventors: Neil Dunski; Ali A. Bazzi, both of Creve Coeur; Henry J. Buehler, St. Louis, all of Mo.

[73] Assignee: Mallinckrodt, Inc., St. Louis, Mo.

[21] Appl. No.: 692,078

[22] Filed: Jan. 17, 1985

[51] Int. Cl.$^4$ ............... C07D 251/30; C07D 251/32; C08K 5/13; C08K 5/24
[52] U.S. Cl. .................... 524/101; 524/291; 544/221; 544/222
[58] Field of Search ........... 544/222, 221; 524/101, 524/291, 302, 304, 305

[56] References Cited

U.S. PATENT DOCUMENTS

| | | | |
|---|---|---|---|
| 3,531,483 | 9/1970 | Gilles | 544/221 |
| 3,679,744 | 7/1972 | Knell et al. | 260/559 |
| 3,707,542 | 12/1972 | Steinberg et al. | 544/221 |
| 3,742,032 | 6/1973 | Beears | 544/221 |
| 4,226,991 | 10/1980 | Nakahara et al. | 544/221 |
| 4,308,195 | 12/1981 | Mayer et al. | 544/221 |
| 4,385,143 | 5/1983 | Yachigo et al. | 544/221 |

*Primary Examiner*—Henry R. Jiles
*Assistant Examiner*—J. G. Mullins
*Attorney, Agent, or Firm*—Richard G. Jackson; Roy J. Klostermann; Lynden N. Goodwin

[57] ABSTRACT

Isocyanurate esters of thioalkanoamidophenols useful in the stabilization of organic materials normally susceptible to oxidative degradation are prepared by reacting an appropriate isocyanurate trithiol, which is a selected tris-mercapto alkanoic acid ester of tris-(2-hydroxyethyl) isocyanurate with an appropriate alkenyl compound, which is a selected N-alkenoyl[4-amino-(mono- or dialkyl)phenol] or, where the alkano moiety is a sole methylene group, by reaction of tris-(2-hydroxyethyl) isocyanurate with an appropriate [mercapto-N-(mono- or di-alkyl-4-hydroxyphenylalkanamide alkenoic] acid. In a preferred embodiment, the ester is 1,3,5-tris{2-hydroxy ethyl-[3-mercapto-(3',5'-di tert-butyl-4'-hydroxypropionanilide)]propionate}isocyanurate.

10 Claims, No Drawings

ISOCYANURATE ESTERS OF THIOAMIDOPHENOLS AND POLYOLEFIN POLYMERIC COMPOSITIONS STABILIZED THEREWITH

This invention relates to isocyanurate esters of thioalkanoamidophenols useful in the stabilization of organic materials normally susceptible to oxidative degradation, a process for preparing the compounds and organic material stabilized with the compounds.

Numerous compounds, including various sterically hindered phenol derivatives, have been proposed for stabilizing organic materials, such as organic polymers, against oxidative and thermal degradation.

Knell et al, U.S. Pat. No. 3,679,744, discloses thiodialkanoamidophenol compounds (more specifically designated as N,N'-bis(alkylhydroxyphenyl)thiaalkanedicarboxamides) obtained by a procedure involving the reaction of a selected alkylaminophenol with a thiodialkanoyl chloride. According to the patent, these monosulfur compounds are useful as stabilizers of organic materials which are subject to oxidative deterioration. Poly-alpha-olefins such as polyethylene, polypropylene, polybutylene, polyisoprene and copolymers thereof are included among the organic materials set forth in the patent. One such monosulfur compound, disclosed in Example I thereof, is N,N'-bis(3',5'-di-t-butyl-4'hydroxyphenyl)2-thiapropane-1,3- dicarboxamide.

Gilles, U.S. Pat. No. 3,531,483, discloses hydroxyphenylalkyleneyl isocyanurates as stabilizers for organic materials. One such compound disclosed therein is tris-(3,5-di-tert-butyl-4-hydroxybenzyl) isocyanurate.

Nakahara et al, U.S. Pat. No. 4,226,991, discloses a process for preparing a polyhydric alcohol 3-alkylthiopropionate polyolefin resin stabilizer. One such compound disclosed therein is 1,3,5-tris-(n-hexylthiopropionyloxyethyl) isocyanurate.

Steinberg et al., U.S. Pat. No. 3,707,542, discloses esters of tris-(hydroxyalkyl) isocyanurates with dialkyl-4-hydroxyphenyl carboxylic acids as stabilizers of organic materials. One such compound disclosed therein is tris-(2-[3-(3,5-di-tert-butyl-4-hydroxyphenyl)propionyloxy]ethyl) isocyanurate.

Beears, U.S. Pat. No. 3,742,032 discloses hexahydro-1,3,5-tris-[beta-(alkylcarboxyalkylthio)propionyl]-s-triazines as stabilizers for polyolefins, particularly polyethylene and polypropylene. One such compound disclosed therein is hexahydro-1,3,5-tris-[beta-(n-dodecyl-2-carboxyethylthio)propionyl]-s-triazine.

However, heretofore known compounds, such as the compounds set forth above, have not been entirely satisfactory for stabilizing organic materials, such as polyolefins (e.g., polyethylene and polypropylene) against oxidative and thermal degradation. Accordingly, there is a substantial need in the art for new compounds having the capability of stabilizing organic materials such as polyethylene and polypropylene against such degradation.

It has now been found that the hereinafter described isocyanurate esters, which are tris-(2-hydroxyethyl) isocyanurate carboxyalkylthioalkanoamidophenol compounds, have such stabilizing capabilities. Such compounds are hereinafter sometimes referred to as THETIS CATA amidophenols or terms of similar import.

DESCRIPTION OF THE INVENTION

Generally stated, the present invention provides THETIS CATA amidophenol compounds which may be represented by Formula I below:

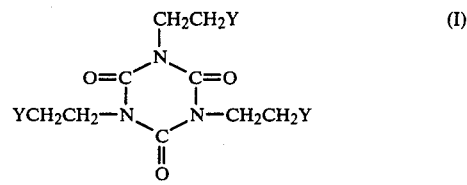

Where Y is a monovalent group represented by Formula II below:

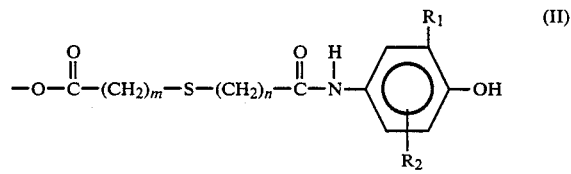

wherein $R_1$ is an alkyl group containing from one to eight carbon atoms or a cycloalkyl group containing from five to 12 carbons atoms; $R_2$ is hydrogen, an alkyl group containing from one to 8 carbon atoms or a cycloalkyl group containing from 5 to 12 carbon atoms; and m is an independently selected integers from 1 to about 10 and n is an independently selected integer from 1 to about 14.

In still another aspect of this invention, there are provided organic compositions of matter stabilized against thermal-oxidative degradation, which comprise an organic material and a stabilizing amount of the compound of Formula I.

DETAILED DESCRIPTION OF THE INVENTION AND OF THE MANNER AND PROCESS OF MAKING AND USING IT

In the compounds of Formula I above where $R_2$ is other than hydrogen, in general each $R_2$ substituent is preferably located ortho to the hydroxyl group on its respective benzene ring, but may be in the meta position.

Suitable alkyl groups from which $R_1$ and $R_2$ may be selected include methyl, ethyl, propyl, isopropyl, butyl, amyl, hexyl, octyl, and the like. Included also are tertiary alkyl groups, such as t-butyl, t-amyl, t-octyl, and the like. Suitable cycloalkyl groups from which $R_1$ and $R_2$ may be selected include cyclopentyl, cyclohexyl, cyclooctyl, cyclododecyl, and the like. Preferably, $R_1$ and $R_2$ are t-butyl groups, with both $R_2$ groups located in their ortho positions. The number of $CH_2$ groups in the compounds is preferably such that each of m and n is 2 in Formula 1 above.

The THETIS CATA amidophenol compounds of this invention include, for example:
(a) 1,3,5-tris-(2-hydroxyethyl-[2-mercapto-(3',5'-di-tert-butyl-4'-hydroxyacetanilide)]acetate) isocyanurate;
(b) 1,3,5-tris-(2-hydroxyethyl-[3-mercapto-(3',5'-di-tert-butyl-4'-hydroxypropionanilide)]propionate) isocyanurate;
(c) 1,3,5-tris-(2-hydroxyethyl-[4-mercapto-(3',5'-di-tert-butyl-4'-hydroxybutyroanilide)]butyrate) isocyanurate;

(d) 1,3,5-tris-(2-hydroxethyl-[5-mercapto-(3', 5'-di-tert-butyl-4'-hydroxypentoanilide)]pent anoate) isocyanuate;
(e) 1,3,5-tris-(2-hydroxyethyl-[3-mercapto-(3', 5'-di-tert-butyl-4'-hydroxyacetanilide)]propionate) isocyanurate;
(f) 1,3,5-tris-(2-hydroxyethyl-[3-mercapto-(3'-tert-butyl-4'-hydroxypropionanilide)]propionate) isocyanurate;
(g) 1,3,5-tris-(2-hydroxyethyl-[3-mercapto-(3'-tert-butyl-5'-methyl-4'-hydroxypropionanilide)}propionate) isocyanurate; and
(h) 1,3,5-tris-(2-hydroxyethyl-[2-mercapto-(3'-tert-butyl-5'-methyl-4'-hydroxyacetanilide)]acetate) isocyanurate.

Preferred compounds of this invention are compounds (a), (b), (c) and (d) above. Compound (b) above is most preferred and corresponds to Formula I above where Y is represented by Formula III below:

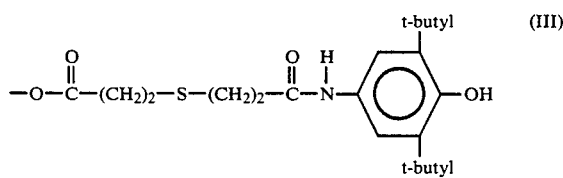

The THETIS CATA amidophenol compounds of this invention can be prepared by reaction of isocyanurate trithiols with alkenes. The reaction is carried out by reacting an appropriate isocyanurate trithiol, i.e. - a selected tris-mercapto ($C_2$–$C_{11}$) alkanoic acid]ester of 1,3,5-tris-(2-hydroxyethyl) isocyanurate, e.g., 1,3,5-tris-[2-hydroxyethyl-(3-mercaptopropionate)]isocyanurate or 1,3,5-tris-[2-hydroxyethyl-(2-mercaptoacetate)-]isocyanurate with an appropriate alkenyl compound, i.e., a selected N-($C_2$–$C_{15}$)alkenoyl[4-amino-(mono- or dialkyl)phenol]containing terminal ene functionality, e.g., N-acryloyl(4-amino-2,6-di-tert-butylphenol). There should be used at least 3 moles of the alkenyl compound per mole of the isocyanurate trithiol.

The reaction is carried out in a solution containing the reactants and at least a solubilizing amount of an inert solvent for at least one, and preferably both, of the reactants and a basic catalyst. Chloroform is preferred as the solvent. When n in formula II is 2, the catalyst can be an alkali metal alkoxide such as sodium methoxide or quarternary ammonium. hydroxide such as trimethylbenzyl ammonium hydroxide (preferred), which is commercially available under the trademark Triton B (Rohm & Haas Co.). When n in formula III is 3 or more, a free radical generator such as a peroxide or an azonitrile preferably azobisisobutyronitrile is used. The catalyst is preferably employed in an amount of about 0.05 gram-mole per one gram-equivalent of available—SH groups of the isocyanurate trithiol.

The reaction may be carried out at any suitable temperature, e.g., about 20°-25° C., and any suitable pressure, e.g., 760 mm Hg, for any suitable period, e.g., from about 0.5 to about 20 hours or more. Although the time required for completion of the reaction is dependent upon the particular reactants and concentrations thereof, catalyst and concentration thereof, solvent, temperature, and pressure employed, the reaction will, in general, be substantially complete within about 1 to about 10 hours.

Advantageously, the reaction is carried out with stirring and under an inert gaseous blanket, i.e., at least substantially inert to the reactants, catalyst, solvent and products employed. Nitrogen is the preferred inert gaseous blanket.

The isocyanurate trithiols for use in the above thiol-alkene reaction can be prepared from tris-(2-hydroxyethyl) isocyanurate and appropriate mercaptoalkanoic acids by well known methods such as the general method set forth in Los, U.S. Pat. No. 3,676,440. The alkenes for use in such reaction can be prepared by amidization of appropriate $C_2$–$C_{15}$ alkenoyl acid halides containing terminal ene functionality, e.g., acrylic acid chloride, with appropriate 4-amino-(mono-or di-alkyl) phenols by well known methods such as the general method described in Dexter, U.S. Pat. No. 4,025,487.

The starting aminophenols can be prepared by general procedures described in U.S. Pat. No. 3,156,690. Advantageously, the aminophenols are prepared by hydrogenating the corresponding nitrosophenols and promptly thereafter reacted in the amidization reaction.

The thiol-alkene reaction set forth above can be (and preferably is) used to prepare those THETIS CATA amidophenol compounds of this invention where n in Formula II above is 2 to 14. However, where n is 1, this reaction is inapplicable.

Where the THETIS CATA amidophenol compounds of this invention have a sole methylene group as the alkano group, i.e., those compounds where n in Formula II is 1, the compounds are prepared by reaction of the triol, tris-(2-hydroxyethyl) isocyanurate, with an appropriate mercapto-N-(mono-or di-alkyl-4-hydroxyphenylalkamide) $C_2$–$C_{11}$ alkenoic]acid, e.g., N-[3,5'-di-tert-butyl-4-hydroxyphenylacetamide-β-mercaptoacetic acid.

Acids for use in the above triol-acid reaction can be prepared by reacting one mole of an appropriate haloacetyl chloride with one mole of a selected alkylaminophenol, e.g., 2,6-di-tert-butyl-4-aminophenol (in the presence of an alkaline material to neutralize hydrogen chloride) followed by treatment of the resulting intermediate with one mole of a thio ($C_2$–$C_{11}$) alkanoic acid in the presence of 2 moles of a suitable alkaline material such as sodium or potassium hydroxide. The desired acid is obtained following neutralization of the sodium salt with dilute acid such as hydrochloric acid.

The compounds of the present invention are useful as stabilizers of organic materials normally subject to oxidative deterioration. Such organic materials include, for example: synthetic organic polymeric substances such as vinyl resins formed from the polymerization of vinyl halides or from the copolymerization of vinyl halides with unsaturated polymerizable compounds, e.g., vinyl esters, α,-β-unsaturated aldehydes and unsaturated hydrocarbons such as butadienes and styrene; poly-alpha-olefins such as polyethylene (e.g., linear low density polyethylene), polypropylene, polybutylene (e.g., polybutene-1), polyisoprene, and the like, including copolymers of polyalpha-olefins, polyurethanes, polyamides such as polyhexamethylene adipamide and polycaprolactam; polyesters such as polymethylene terephthalates; polycarbonates, polyacetals; polystyrene; polyethyleneoxide; and copolymers such as those of high impact polystyrene containing copolymers of butadiene and styrene and those formed by the copolymerization of acrylonitrile, butadiene and/or styrene. Other materials which can be stabilized by the active compounds of the present invention include lubrication oil of the aliphatic ester type, i.e., di(2-ethylhexyl)-azelate, pentaerythritol tetracaproate, and the like; animal and vegetable derived oils, e.g., linseed oil, fat, tallow, lard, peanut oil, cod liver oil, castor oil, palm oil, corn oil, cotton-seed oil, and the like; hydrocarbon materials such as gasoline, mineral oil, fuel oil, drying oil, cutting fluids, waxes, resins and the like, fatty acids, soaps and the like.

The compounds of this invention (represented by Formula I above) may be employed in any stabilizing amount as stabilizers for organic materials normally susceptible to oxidative degradation. Such amount may be for example, from about 0.005% to about 10% by weight of the stabilized composition. For polyolefins, e.g., linear low density polyethylene, polypropylene and poly(butene-1), such amount is preferably from about 0.05% to about 5% and more preferably from about 0.1% to about 1%.

The compounds of this invention may be used alone or in combination with other stabilizers or additive materials, such as dilauryl-beta-thiodipropionate and distearyl-beta-thiodipropionate.

Other antioxidants, antiozonants, thermal stabilizers, ultraviolet light absorbers, coloring materials, dyes, pigments, metal chelating agents, etc. may also be used in the compositions of the invention.

Phosphite esters may also be used in stabilized compositions containing the novel antioxidant compounds of the present invention. Such phosphite esters include dialkyl phosphites (for example, distearyl phosphite, dilauryl phosphite, and the like e.g., trialkyl phosphites (for example, trilauryl phosphite, tris(ethylhexyl) phosphite, and the like); and tris(alkaryl) phosphites (for example tris(nonylphenyl)phosphites, and the like).

The compounds of this invention are especially useful for stabilizing polymeric materials such as polyolefins and the like, e.g., polyethylene (especially linear low density polyethylene, i.e., LLDPE), polypropylene, poly(butene-1), and the like.

Stabilized compositions of matter of this invention may be prepared by incorporating the compounds into the organic material to be stabilized using well known methods for incorporating stabilizers into such material. For example, in general, the stabilizer may simply be physically admixed with the organic material.

It is well known that upon processing polyethylenes at elevated temperature, cross-linking takes place. This results in an apparent increase in molecular weight and hence lower melt index values. More importantly, it also results in a change in molecular weight distribution by increasing, due to cross-linking the high molecular weight tail. In many applications, it is desired that polyethylene not cross-link while being processed. Accordingly, a feature of a good stabilizer is that the melt index does not appreciably decrease when working a polyethylene as in extrusion operations.

In contrast to polyethylenes, polypropylene typically undergoes chain scission during processing thereof at elevated temperatures, i.e., a reduction in apparent molecular weight. This is reflected typically in melt flow rate values which increase as the molecular weight decreases.

Practice of the present invention is illustrated by the following non-limiting examples. All parts, percents and other amounts given throughout this disclosure, including the examples which follow, are by weight unless otherwise indicated.

EXAMPLE 1

A solution of thioglycolic acid (7.36 g, 0.08 mole) in 100 ml ethanol was added to 160 ml of aqueous sodium hydroxide (6.4 g, 0.16 mole). To the resulting clear solution was slowly added N-(3,5-di-tert-butyl-4-hydroxyphenyl)chloroacetamide (23.8 g, 0.08 mole) in 500 ml ethanol. A slight exotherm was observed and the mixture turned brown toward the end of the addition. Stirring continued for another 2 hrs. The resulting dark brown solution was diluted with an equal volume of water and neutralized to a pH of 3.4. Additional water was added to effect precipitation of a tan colored solid material. After collecting the solid product by filtration, it was washed with boiling toluene to yield shiny white crystals of N-[(3,5-di-tert-butyl-4-hydroxyphenyl)acetamide]-$\beta$-mercaptoacetic acid, melting point 170° C., yield 22.56 g (80%.). A mixture of N-[(3,5-di-tert-butyl-4-hydroxyphenylacetamide]-$\beta$-mercaptoacetic acid (8.35 g, 0.023 mole) and tris-(2-hydroxyethyl) isocyanurate (2.05 g, 0.007 mole) was dissolved in 300 ml of toluene in a reactor equipped with a stirrer, condenser and Dean-Stark trap. After p-toluenesulfonic acid monohydrate (0.4 g) was added, the mixture was refluxed with stirring under a nitrogen atmosphere until the theoretical amount of water was collected in the Dean-Stark trap. At the end of the reflux period, the resulting yellowish mixture was cooled, filtered and washed successively with water, aqueous 0.5% NaOH and saturated NaCl. After drying over anhydrous MgSO$_4$, the solvent was removed in vacuo to give a white solid, melting point 98°–100° C. (toluene/hexane), yield 85%.

The product was identified as 1,3,5-tris-(2-hydroxyethyl-[2-mercapto-(3', 5'-di-tert-butyl-4'-hydroxyacetanilide]acetate) isocyanurate on the basis of IR, $^1$H and $^{13}$C NMR spectroscopic analyses.

EXAMPLE 2

In a reactor equipped with a stirrer, a mixture of 2.75 g (0.01 mole) N-acryloyl(4-amino-2,6-di-tert-butylphenol), 1.74 g (0.003 mole) tris-(2-ethyl-3-mercaptopropionyl) isocyanurate, 0.4 ml of trimethylbenzyl ammonium hydroxide (Triton B, Rohm & Haas Co.) and 55 ml CHCl$_3$ as solvent was stirred for 4 hours. After the reaction was complete, 5 ml of glacial acetic acid was added to neutralize the solution. Ater washing with water and drying over anhydrous MgSO$_4$, the solvent was removed by evaporation under reduced pressure to leave a yellow solid, which was recrystallized from 2-propanol/H$_2$O.

The white crystalline solid, m.p. 85°–87° C., 83% yield was identified by IR, $^1$H and $^{13}$C NMR spectra to be 1,3,5-tris-(2-hydroxyethyl-[3-mercapto-(3', 5'-di-tert-butyl-4'-hydroxypropionanilide)]propionate) isocyanurate.

EXAMPLE 3

The procedure of Example 1 was repeated in all its essential features except as follows: the isocyanurate starting material was 1,3,5-tris-(2-hydroxyethyl-(2-mercaptoacetate)]isocyanurate (3.22 g, 0.006 mole), the amount of the N-acryloyl reactant added was 5.5 g (0.02 mole), 60 ml of chloroform and 5 ml of Triton B were used, the reaction mixture was stirred overnight (about 12 to 16 hours) and 6 ml of acetic acid was used for neutralization. After solvent removal, there was obtained a white solid, m.p. 115° C. (toluene), yield 82%.

The product was identified as 1,3,5-tris-(2-hydroxyethyl-[3-mercapto-(3', 5'-di-tert-butyl-4'-hydroxyacetanilide)]propionate) isocyanurate on the basis of IR, $^1$H and $^{13}$C NMR spectra.

EXAMPLE 4

Linear Low Density Polyethylene

In this Example, the compounds of Examples 1, 2 and 3 (hereinafter Compounds I, II, and III, respectively, were tested for capability of stabilizing linear low density polyethylene (LLDPE) against oxidative and thermal degradation. For comparative purposes, a test sample of the LLDPE to which no compound was added was also tested. 0.7 g of each of Compounds I, II and III was blended with a separate sample (700 g) of the LLDPE (melt index 1.0, Union Carbide Corporation) devoid of any added antioxidant. Each of the resulting blends as well as the LLDPE without any antioxidant added was extruded twice at 160° C. in a ¾" Brabender extruder. The extruder speed was set at 50 rpm. Each extruded rod was pelletized prior to reextrusion. Following the two compounding passes at 160° C. each sample was extruded 5 times at 260° C. and 50 rpm, with each extruded rod being water quenched and pelletized prior to reextrusion. The melt index was then determined according to ASTM D1238 condition E (190° C., 2160 g) on each of the pelletized samples following the first, third and fifth extrusions at 260° C. Samples from the second extrusion at 160° C. were compression molded at 170° C. and 10 tons pressure into plaques of 25 mils thickness.

Twelve chips, each about 1 inch in diameter, were cut from each plaque and placed in a 150° C. air circulating oven. Time to degradation was determined for these chips. As is well known to those skilled in the art, the "time to degradation" in such oven aging test is the time at which substantially the entire sample becomes discolored and brittle.

The following results were obtained:

| Antioxidant | Melt Index, g/10 min. ASTM D1238 Condition E | | | Hours To Degradation at 150° C. |
|---|---|---|---|---|
| | 1st Extrusion at 260° C. | 3rd Extrusion at 260° C. | 5th Extrusion at 260° C. | |
| None | 0.61 | 0.38 | 0.29 | 24 |
| Compound I | 0.92 | 0.92 | 0.89 | 168 |
| Compound II | 0.99 | 0.95 | 0.89 | 216 |
| Compound III | 1.01 | 0.97 | 0.93 | 72 |

The results show very good retention of melt index during processing as well as very good long term oven stability for Compounds I, II and III.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. An ethyl isocyanurate carboxyalkylthioalkanoamidophenol compound having the following formula I:

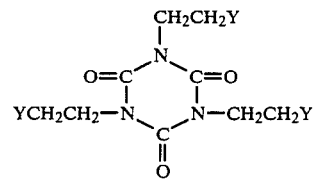

where Y is a monovalent group having the following Formula II:

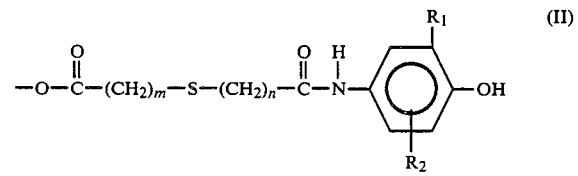

where $R_1$ is an alkyl group containing from one to eight carbon atoms or a cycloalkyl group containing from five to 12 carbon atoms; $R_2$ is hydrogen, an alkyl group containing from one to eight carbon atoms or a cycloalkyl group containing from 5 to 12 carbon atoms; and m is selected integer from 1 to about 10 and n is a selected integer from 1 to about 14.

2. The compound of claim 1 wherein $R_1$ and $R_2$ are tertiary alkyl groups.

3. The compound of claim 1 wherein $R_1$ and $R_2$ are tertiary butyl groups.

4. The compound of claim 1: 1,3,5-tris-(2-hydroxyethyl-[2-mercapto-(3', 5'-di-tert-butyl-4'-hydroxyacetanilide)]acetate) isocyanurate.

5. The compound of claim 1: 1,3,5-tris-(2-hydroxyethyl-[3-mercapto-(3', 5'-di-tert-butyl-4'-hydroxypropionanilide)]propionate) isocyanurate.

6. The compound of claim 1: 1,3,5-tris-(2-hydroxyethyl-[3-mercapto-(3', 5'-di-tert-butyl-4'-hydroxyacetanilide)]propionate) isocyanurate.

7. A composition of matter comprising a polyolefin normally subject to oxidative deterioration and a stabilizing amount of the compound of claim 1, 2, 3, 4, 5 or 6.

8. A composition of matter comprising linear low density polyethylene and a stabilizing amount of the compound of claim 1, 2, 3, 4, 5 or 6.

9. A composition of matter comprising polypropylene and a stabilizing amount of the compound of claim 1, 2, 3, 4, 5 or 6.

10. A composition of matter comprising poly(butene-1) and a stabilizing amount of the compound of claim 1, 2, 3, 4, 5 or 6.

* * * * *